US011679248B2

(12) United States Patent
Lareau et al.

(10) Patent No.: US 11,679,248 B2
(45) Date of Patent: Jun. 20, 2023

(54) PRESSURE ACTIVATED VALVE FOR HIGH FLOW RATE AND PRESSURE VENOUS ACCESS APPLICATIONS

(71) Applicant: ANGIODYNAMICS, INC., Latham, NY (US)

(72) Inventors: Raymond Lareau, Westford, MA (US); Mark Girard, Medway, MA (US); Benjamin Bell, Shrewsbury, MA (US)

(73) Assignee: ANGIODYNAMICS, INC., Latham, NY (US)

( * ) Notice: Subject to any disclaimer, the term of this patent is extended or adjusted under 35 U.S.C. 154(b) by 513 days.

(21) Appl. No.: 15/240,430

(22) Filed: Aug. 18, 2016

(65) Prior Publication Data

US 2016/0354599 A1 Dec. 8, 2016
US 2023/0029443 A9 Jan. 26, 2023

Related U.S. Application Data

(63) Continuation of application No. 13/566,386, filed on Aug. 3, 2012, now Pat. No. 9,447,892, which is a
(Continued)

(51) Int. Cl.
*A61M 39/24* (2006.01)
*F16K 15/14* (2006.01)
*F16K 27/02* (2006.01)

(52) U.S. Cl.
CPC ............ *A61M 39/24* (2013.01); *F16K 15/147* (2013.01); *F16K 27/0209* (2013.01);
(Continued)

(58) Field of Classification Search
CPC .......... A61M 39/24; A61M 2039/2426; A61M 2039/242; A61M 2039/064; A61M 39/06;
(Continued)

(56) References Cited

U.S. PATENT DOCUMENTS 26,235 A 11/1859 Scott
500,745 A 7/1893 Rogers
(Continued)

FOREIGN PATENT DOCUMENTS

CN 102155808 8/2011
DE 3048203 7/1982
(Continued)

OTHER PUBLICATIONS

Biffi, et al, A Randomized, Prospective Trial of Central Venous Ports Connected to Standard Open-Ended or Groshong Catheters in Adault Oncology Patients, American Cancer Society, 2001, pp. 1204-1212.
(Continued)

*Primary Examiner* — Jason E Flick
(74) *Attorney, Agent, or Firm* — DLA Piper LLP (US)

(57) ABSTRACT

A valve comprises a first housing including a first lumen extending therethrough and defining a first disk-facing surface and a second housing including a second lumen extending therethrough and defining a second disk-facing surface, the second housing being mated to the first housing so that the second disk-facing surface faces the first disk-facing surface in combination with a flexible disk gripped between gripping portions of the first and second disk-facing surfaces, the disk including a slit extending therethrough which, when acted upon by a fluid pressure of at least a predetermined threshold level opens to permit fluid flow between the first and second lumens and which, when acted upon by a fluid pressure less than the threshold level remains sealed preventing fluid flow between the first and second lumens and a relief well between opposing portions of the first and second housings radially outside the gripping portions, a width of the relief well exceeding a width of a radially outer
(Continued)

portion of the flexible disk so that the radially outer portion of the disk is free to move therewithin.

20 Claims, 7 Drawing Sheets

Related U.S. Application Data continuation of application No. 12/124,589, filed on May 21, 2008, now Pat. No. 8,257,321.

(52) U.S. Cl.
CPC ............... *A61M 2039/246* (2013.01); *A61M 2039/2426* (2013.01); *Y10T 137/7881* (2015.04)

(58) Field of Classification Search
CPC ............ A61M 2039/246; A61M 39/22; A61M 2039/2446; A61M 2039/2433; A61M 2039/244; F16K 15/147; F16K 27/0209; F16K 15/14; F16K 15/144
See application file for complete search history.

(56) References Cited

U.S. PATENT DOCUMENTS

| | | |
|---|---|---|
| 1,142,525 A | 6/1915 | Maag |
| 1,244,379 A | 10/1917 | Short |
| 1,989,145 A | 1/1935 | Newby |
| 2,122,299 A | 6/1938 | Sloan |
| 2,446,571 A | 8/1948 | Browne |
| 2,720,881 A | 10/1955 | Jones |
| 2,755,060 A | 7/1956 | Twyman |
| 2,841,166 A | 7/1958 | Auzin |
| 3,020,913 A | 2/1962 | Heyer |
| 3,111,125 A | 11/1963 | Schulte |
| 3,113,586 A | 12/1963 | Edmark |
| 3,118,468 A | 1/1964 | Bochan |
| 3,159,175 A | 12/1964 | Macmillan |
| 3,159,176 A | 12/1964 | Gifford et al. |
| RE26,235 E | 7/1967 | Woodford |
| 3,422,844 A | 1/1969 | Grise |
| 3,477,438 A | 11/1969 | Allen et al. |
| 3,514,438 A | 5/1970 | Bixler et al. |
| 3,525,357 A | 8/1970 | Koreski |
| 3,621,557 A | 11/1971 | Cushman et al. |
| 3,662,955 A | 5/1972 | Takanashi |
| 3,669,323 A | 6/1972 | Harker et al. |
| 3,673,612 A | 7/1972 | Merill et al. |
| 3,674,183 A | 7/1972 | Venable et al. |
| 3,710,942 A | 1/1973 | Rosenberg |
| 3,788,327 A | 1/1974 | Donowitz et al. |
| 3,811,466 A | 5/1974 | Ohringer |
| 3,827,456 A | 8/1974 | Sheppard |
| 3,848,579 A | 11/1974 | Villa-Real |
| 3,885,561 A | 5/1975 | Cami |
| 3,888,249 A | 6/1975 | Spencer |
| 3,941,149 A | 3/1976 | Mittleman |
| 3,955,594 A | 5/1976 | Snow |
| 3,964,509 A | 6/1976 | Daubenberger |
| 4,000,740 A | 1/1977 | Mittleman |
| 4,072,146 A | 2/1978 | Howes |
| 4,134,402 A | 1/1979 | Mahurkar |
| 4,137,152 A | 1/1979 | Chester |
| 4,142,525 A | 3/1979 | Binard et al. |
| 4,143,853 A * | 3/1979 | Abramson ............ A61M 39/26 137/515.7 |
| 4,176,678 A | 12/1979 | Le Cun |
| 4,232,677 A | 11/1980 | Leibinsohn |
| 4,244,379 A | 1/1981 | Smith |
| 4,327,722 A | 5/1982 | Groshong |
| 4,342,315 A | 8/1982 | Jackson |
| 4,387,879 A | 6/1983 | Tauschinski |
| 4,405,316 A | 9/1983 | Mittleman |
| 4,417,888 A | 11/1983 | Cosentino |
| 4,424,058 A | 1/1984 | Parsons |
| 4,424,833 A * | 1/1984 | Spector ............ A61M 39/0606 128/202.15 |
| 4,431,426 A | 2/1984 | Groshong |
| 4,434,810 A | 3/1984 | Atkinson |
| 4,447,237 A | 5/1984 | Frisch et al. |
| 4,465,102 A | 8/1984 | Rupp |
| 4,468,224 A | 8/1984 | Enzmann et al. |
| 4,475,898 A | 10/1984 | Brodner |
| 4,502,502 A | 3/1985 | Krug |
| 4,524,805 A | 6/1985 | Hoffman |
| 4,529,399 A | 7/1985 | Groshong |
| 4,543,087 A | 9/1985 | Sommercorn et al. |
| 4,549,879 A | 10/1985 | Groshong |
| 4,552,553 A | 11/1985 | Schulte et al. |
| 4,559,046 A | 12/1985 | Groshong |
| 4,610,276 A | 9/1986 | Paradis |
| 4,610,665 A | 9/1986 | Matsumoto et al. |
| 4,616,768 A | 10/1986 | Flier |
| 4,625,245 A | 11/1986 | White |
| 4,626,245 A | 12/1986 | Weinstein |
| 4,646,945 A * | 3/1987 | Steiner ............... A47K 5/1209 222/215 |
| 4,668,221 A | 5/1987 | Luther |
| 4,671,796 A | 6/1987 | Groshong |
| 4,673,393 A | 6/1987 | Suzuki et al. |
| 4,681,572 A | 7/1987 | Tokarz et al. |
| 4,692,141 A | 9/1987 | Mahurkar |
| 4,692,146 A | 9/1987 | Hilger |
| 4,701,166 A | 10/1987 | Groshong |
| 4,722,725 A | 2/1988 | Sawyer et al. |
| 4,728,006 A | 3/1988 | Drobish |
| 4,737,152 A | 4/1988 | Alchas |
| 4,753,640 A | 6/1988 | Nichols |
| 4,790,817 A | 12/1988 | Luther |
| 4,790,832 A | 12/1988 | Lopez |
| 4,798,594 A | 1/1989 | Hillstead |
| 4,801,297 A | 1/1989 | Mueller |
| 4,809,679 A | 3/1989 | Shimonaka |
| 4,813,934 A | 3/1989 | Engelson |
| 4,842,591 A | 6/1989 | Luther |
| 4,908,028 A | 3/1990 | Colon et al. |
| 4,944,726 A | 7/1990 | Hilal et al. |
| 4,946,448 A * | 8/1990 | Richmond ............ A61M 39/24 137/493.9 |
| 4,950,252 A | 8/1990 | Luther |
| 4,960,412 A | 10/1990 | Fink |
| 4,973,319 A | 11/1990 | Melsky |
| 4,986,814 A | 1/1991 | Burney |
| 4,991,745 A | 2/1991 | Brown |
| 4,994,046 A | 2/1991 | Wesson |
| 4,995,863 A | 2/1991 | Nichols |
| 4,998,919 A | 3/1991 | Schnepp-Pesch |
| 5,000,745 A * | 3/1991 | Guest ............... A61M 39/0606 604/256 |
| 5,009,391 A | 4/1991 | Steigerwald |
| 5,030,210 A | 7/1991 | Alchas |
| 5,062,836 A | 11/1991 | Wendell |
| 5,084,015 A | 1/1992 | Moriuchi |
| 5,085,635 A | 2/1992 | Cragg |
| 5,098,405 A | 3/1992 | Peterson et al. |
| 5,125,893 A | 6/1992 | Dryden |
| 5,143,853 A | 9/1992 | Walt |
| 5,147,332 A | 9/1992 | Moorehead |
| 5,149,327 A | 9/1992 | Oshiyama |
| 5,167,638 A | 12/1992 | Felix et al. |
| 5,169,393 A | 12/1992 | Moorehead et al. |
| 5,176,652 A | 1/1993 | Littrell |
| 5,176,662 A | 1/1993 | Bartholomew et al. |
| 5,201,722 A * | 4/1993 | Moorehead ............ A61M 39/22 604/247 |
| 5,201,772 A | 4/1993 | Maxwell |
| 5,205,834 A | 4/1993 | Moorehead et al. |
| 5,215,538 A | 6/1993 | Larkin |
| 5,249,598 A | 10/1993 | Schmidt |
| 5,253,765 A | 10/1993 | Moorehead et al. |
| 5,254,086 A | 10/1993 | Palmer et al. |

(56) References Cited

U.S. PATENT DOCUMENTS

| | | | |
|---|---|---|---|
| 5,255,676 A | 10/1993 | Russo | |
| 5,324,274 A | 6/1994 | Martin | |
| 5,330,424 A | 7/1994 | Palmer et al. | |
| 5,336,203 A | 8/1994 | Goldhardt et al. | |
| 5,360,407 A | 11/1994 | Leonard et al. | |
| 5,370,624 A | 12/1994 | Edwards et al. | |
| 5,395,352 A | 3/1995 | Penny | |
| 5,396,925 A | 3/1995 | Poli | |
| 5,399,168 A | 3/1995 | Wadsworth, Jr. et al. | |
| 5,401,255 A | 3/1995 | Sutherland et al. | |
| D357,735 S | 4/1995 | McPhee | |
| 5,405,340 A | 4/1995 | Fageol et al. | |
| 5,411,491 A | 5/1995 | Goldhardt et al. | |
| 5,453,097 A * | 9/1995 | Paradis | A61M 39/24 |
| | | | 604/86 |
| 5,454,784 A | 10/1995 | Atkinson et al. | |
| 5,469,805 A | 11/1995 | Gibbs | |
| 5,470,305 A | 11/1995 | Arnett et al. | |
| 5,484,420 A | 1/1996 | Russo | |
| 5,542,923 A | 8/1996 | Ensminger et al. | |
| 5,545,150 A | 8/1996 | Danks et al. | |
| 5,554,136 A | 9/1996 | Luther | |
| 5,562,618 A | 10/1996 | Cai et al. | |
| 5,571,093 A | 11/1996 | Cruz et al. | |
| 5,575,769 A | 11/1996 | Vaillancourt | |
| 5,619,393 A | 4/1997 | Summerfelt | |
| 5,624,395 A | 4/1997 | Mikhail et al. | |
| 5,637,099 A | 6/1997 | Durdin et al. | |
| 5,667,500 A | 9/1997 | Palmer et al. | |
| 5,707,357 A | 1/1998 | Mikhail et al. | |
| 5,743,873 A | 4/1998 | Cai et al. | |
| 5,743,884 A | 4/1998 | Hasson et al. | |
| 5,743,894 A | 4/1998 | Swisher | |
| 5,752,928 A | 5/1998 | de Roulhac et al. | |
| 5,752,938 A | 5/1998 | Flatland et al. | |
| 5,769,107 A | 6/1998 | Woodruff | |
| 5,803,078 A | 9/1998 | Brauner | |
| 5,807,349 A | 9/1998 | Person et al. | |
| 5,810,789 A | 9/1998 | Powers et al. | |
| 5,843,044 A | 12/1998 | Moorehead | |
| 5,853,397 A | 12/1998 | Shemesh et al. | |
| 5,858,003 A | 1/1999 | Atala | |
| 5,865,308 A | 2/1999 | Qin et al. | |
| 5,868,703 A | 2/1999 | Bertolero | |
| 5,944,698 A | 8/1999 | Fischer et al. | |
| 5,984,902 A | 11/1999 | Moorehead | |
| 5,989,233 A | 11/1999 | Yoon | |
| 6,033,393 A | 3/2000 | Balbierz et al. | |
| 6,045,734 A | 4/2000 | Luther et al. | |
| 6,050,934 A | 4/2000 | Mikhail et al. | |
| 6,056,717 A | 5/2000 | Finch et al. | |
| 6,062,244 A | 5/2000 | Arkans | |
| 6,081,106 A | 6/2000 | Camerlo | |
| 6,092,551 A | 7/2000 | Bennett | |
| 6,099,505 A | 8/2000 | Ryan et al. | |
| 6,110,154 A | 8/2000 | Shimomura | |
| 6,120,483 A | 9/2000 | Davey et al. | |
| 6,152,129 A | 11/2000 | Berthon-Jones | |
| 6,152,909 A | 11/2000 | Bagaoisan et al. | |
| 6,167,886 B1 | 1/2001 | Engel et al. | |
| 6,171,287 B1 | 1/2001 | Lynn | |
| 6,210,366 B1 | 4/2001 | Sanfilippo, II | |
| 6,227,200 B1 | 5/2001 | Crump et al. | |
| 6,270,489 B1 | 8/2001 | Wise et al. | |
| 6,296,316 B1 | 10/2001 | Hann | |
| 6,306,124 B1 | 10/2001 | Jones et al. | |
| 6,322,541 B2 * | 11/2001 | West | A61M 39/0606 |
| | | | 137/844 |
| 6,364,861 B1 | 4/2002 | Feith et al. | |
| 6,364,867 B2 | 4/2002 | Wise et al. | |
| 6,375,637 B1 | 4/2002 | Campbell et al. | |
| 6,415,793 B1 | 7/2002 | Kretz | |
| 6,436,077 B1 | 8/2002 | Davey et al. | |
| 6,442,415 B1 | 8/2002 | Bis et al. | |
| 6,446,671 B2 | 9/2002 | Armenia et al. | |
| 6,508,791 B1 | 1/2003 | Guerrero | |
| 6,551,270 B1 | 4/2003 | Bimbo et al. | |
| 6,610,031 B1 | 8/2003 | Chin | |
| 6,726,063 B2 | 4/2004 | Stull et al. | |
| 6,786,884 B1 | 9/2004 | DeCant, Jr. et al. | |
| 6,874,999 B2 | 4/2005 | Dai et al. | |
| 6,929,631 B1 | 8/2005 | Brugger et al. | |
| 6,953,450 B2 | 10/2005 | Baldwin et al. | |
| 6,994,314 B2 | 2/2006 | Garnier et al. | |
| 7,025,744 B2 | 4/2006 | Utterberg | |
| 7,081,106 B1 | 7/2006 | Guo et al. | |
| 7,252,652 B2 | 8/2007 | Moorehead et al. | |
| 7,291,133 B1 | 11/2007 | Kindler et al. | |
| 7,316,655 B2 | 1/2008 | Garibotto et al. | |
| 7,435,236 B2 | 10/2008 | Weaver | |
| D595,846 S | 7/2009 | Racz | |
| D596,288 S | 7/2009 | Racz | |
| 7,601,141 B2 | 10/2009 | Dikeman | |
| 7,637,893 B2 | 12/2009 | Christensen | |
| 7,713,250 B2 | 5/2010 | Harding | |
| 7,731,700 B1 | 6/2010 | Schytte | |
| 7,758,541 B2 | 7/2010 | Wallace | |
| 7,931,619 B2 | 4/2011 | Diamond | |
| 7,947,032 B2 | 5/2011 | Harding | |
| 7,951,121 B2 | 5/2011 | Weaver | |
| 7,988,679 B2 | 8/2011 | Daly | |
| 7,993,327 B2 | 8/2011 | Casey, II | |
| D644,731 S | 9/2011 | Fangrow, Jr. | |
| 8,034,035 B2 | 10/2011 | Weaver | |
| 8,079,987 B2 | 12/2011 | Moorehead | |
| 8,083,721 B2 | 12/2011 | Miller | |
| 8,105,314 B2 | 1/2012 | Fangrow, Jr. | |
| 8,187,234 B2 | 5/2012 | Weaver | |
| 8,257,321 B2 * | 9/2012 | Lareau | A61M 39/24 |
| | | | 604/167.04 |
| 8,291,936 B2 * | 10/2012 | Carmody | F16K 15/144 |
| | | | 137/859 |
| 8,328,768 B2 | 12/2012 | Quigley | |
| 8,337,470 B2 | 12/2012 | Prasad | |
| 8,343,113 B2 | 1/2013 | Hokanson | |
| 8,377,011 B2 | 2/2013 | Weaver | |
| 8,398,607 B2 | 3/2013 | Fangrow, Jr. | |
| 8,444,628 B2 | 5/2013 | Fangrow, Jr. | |
| 8,454,574 B2 | 6/2013 | Weaver | |
| 8,454,579 B2 | 6/2013 | Fangrow, Jr. | |
| 8,523,821 B2 | 9/2013 | Miller | |
| 8,529,523 B2 | 9/2013 | Weaver | |
| 8,540,685 B2 | 9/2013 | Moorehead | |
| 8,585,660 B2 | 11/2013 | Murphy | |
| 8,603,070 B1 | 12/2013 | Lareau | |
| 8,628,515 B2 | 1/2014 | Fangrow, Jr. | |
| 8,679,074 B2 | 3/2014 | Daly | |
| 8,726,931 B2 | 5/2014 | Buiser | |
| 8,753,320 B2 | 6/2014 | Miller | |
| 8,758,306 B2 | 6/2014 | Lopez | |
| 8,784,402 B1 | 7/2014 | Lareau | |
| 8,789,558 B2 | 7/2014 | Volker | |
| 8,870,850 B2 | 10/2014 | Fangrow, Jr. | |
| 8,876,797 B2 | 11/2014 | Lareau | |
| 8,926,571 B1 | 1/2015 | Keith | |
| D722,155 S | 2/2015 | Wiegel | |
| D722,156 S | 2/2015 | Wiegel | |
| D722,157 S | 2/2015 | Wiegel | |
| 9,044,541 B2 | 6/2015 | Blanchard | |
| 9,186,494 B2 | 11/2015 | Fangrow | |
| 9,192,753 B2 | 11/2015 | Lopez | |
| 9,192,755 B2 | 11/2015 | Ravenscroft | |
| 9,205,243 B2 | 12/2015 | Lopez | |
| 9,206,283 B1 | 12/2015 | Santerre | |
| 9,238,129 B2 | 1/2016 | Fangrow, Jr. | |
| D752,215 S | 3/2016 | Blennnow | |
| 9,278,206 B2 | 3/2016 | Fangrow | |
| D757,259 S | 5/2016 | Duck | |
| 9,447,892 B2 * | 9/2016 | Lareau | A61M 39/24 |
| 10,500,329 B2 | 12/2019 | Weaver | |
| 2001/0023333 A1 | 9/2001 | Wise et al. | |
| 2001/0037079 A1 | 11/2001 | Burbank et al. | |
| 2002/0010425 A1 | 1/2002 | Guo et al. | |
| 2002/0016584 A1 | 2/2002 | Wise et al. | |

(56) References Cited

U.S. PATENT DOCUMENTS

| | | |
|---|---|---|
| 2002/0026145 A1 | 2/2002 | Bagaoisan |
| 2002/0111662 A1 | 8/2002 | Iaizzo |
| 2002/0121530 A1 | 9/2002 | Socier |
| 2002/0156430 A1 | 10/2002 | Haarala et al. |
| 2002/0157664 A1 | 10/2002 | Fugelsang et al. |
| 2002/0165492 A1 | 11/2002 | Davey et al. |
| 2002/0193752 A1 | 12/2002 | Lynn |
| 2003/0014015 A1 | 1/2003 | Tansey |
| 2003/0122095 A1 | 7/2003 | Wilson et al. |
| 2003/0189067 A1 | 10/2003 | Stull |
| 2003/0195478 A1 | 10/2003 | Russo |
| 2004/0034324 A1 | 2/2004 | Seese et al. |
| 2004/0064128 A1 | 4/2004 | Raijman et al. |
| 2004/0102738 A1 | 5/2004 | Dikeman et al. |
| 2004/0108479 A1 | 6/2004 | Garnier et al. |
| 2004/0186444 A1 | 9/2004 | Daly et al. |
| 2004/0193119 A1 | 9/2004 | Canaud et al. |
| 2004/0210194 A1 | 10/2004 | Bonnette et al. |
| 2004/0267185 A1 | 12/2004 | Weaver et al. |
| 2005/0010176 A1 | 1/2005 | Dikeman et al. |
| 2005/0027261 A1 | 2/2005 | Weaver et al. |
| 2005/0043703 A1 | 2/2005 | Nordgren |
| 2005/0049555 A1 | 3/2005 | Moorehead et al. |
| 2005/0149116 A1 | 7/2005 | Edwards et al. |
| 2005/0165364 A1 | 7/2005 | DiMatteo et al. |
| 2005/0171488 A1 | 8/2005 | Weaver et al. |
| 2005/0171490 A1 | 8/2005 | Weaver et al. |
| 2005/0171510 A1 | 8/2005 | DiCarlo et al. |
| 2005/0283122 A1 | 12/2005 | Nordgren |
| 2006/0129092 A1 | 6/2006 | Hanlon et al. |
| 2006/0135949 A1 | 6/2006 | Rome et al. |
| 2006/0149189 A1 | 7/2006 | Diamond et al. |
| 2006/0149211 A1 | 7/2006 | Simpson et al. |
| 2006/0149214 A1 | 7/2006 | Breiter et al. |
| 2007/0161940 A1 | 7/2007 | Blanchard et al. |
| 2007/0161970 A1 | 7/2007 | Spohn et al. |
| 2007/0163664 A1* | 7/2007 | Mijers .................. A61M 39/24 137/859 |
| 2007/0276313 A1 | 11/2007 | Moorehead et al. |
| 2008/0097341 A1 | 4/2008 | Casey |
| 2008/0108956 A1 | 5/2008 | Lynn et al. |
| 2008/0200837 A1 | 8/2008 | Frazier |
| 2009/0177187 A1 | 7/2009 | Weaver Quigley |
| 2009/0292252 A1 | 11/2009 | Lareau |
| 2011/0062703 A1 | 3/2011 | Lopez |
| 2011/0087093 A1 | 4/2011 | Buiser |
| 2011/0118612 A1 | 5/2011 | Miller |
| 2011/0264054 A1 | 10/2011 | Miller |
| 2011/0313367 A1 | 12/2011 | Daly |
| 2011/0313368 A1 | 12/2011 | Weaver |
| 2012/0271247 A1 | 10/2012 | Weaver |
| 2012/0325351 A1 | 12/2012 | Volker |
| 2013/0060200 A1 | 3/2013 | Dalton |
| 2013/0220462 A1 | 8/2013 | Lareau |
| 2013/0338608 A1 | 12/2013 | Moorehead |
| 2014/0081285 A1 | 3/2014 | Kucklick |
| 2014/0163516 A1 | 6/2014 | Lareau |
| 2015/0135554 A1 | 5/2015 | Smith |
| 2016/0008530 A1 | 1/2016 | Weaver |
| 2016/0121041 A1 | 5/2016 | Weaver |

FOREIGN PATENT DOCUMENTS

| | | |
|---|---|---|
| DE | 20208420 | 5/2008 |
| EP | 0128525 | 12/1984 |
| EP | 0128625 | 12/1984 |
| EP | 0198962 | 10/1986 |
| EP | 0337617 | 10/1989 |
| EP | 0366814 | 5/1990 |
| EP | 0474069 | 3/1992 |
| EP | 0864336 | 9/1998 |
| EP | 0882466 | 12/1998 |
| EP | 0930082 | 7/1999 |
| EP | 1016431 | 7/2000 |
| EP | 2720881 | 4/2014 |
| EP | 2755060 | 7/2014 |
| FR | 2508008 | 12/1982 |
| FR | 2718969 | 10/1995 |
| GB | 2102398 | 2/1983 |
| JP | S576863 | 1/1982 |
| JP | S59133877 | 8/1984 |
| JP | S6088562 | 5/1985 |
| JP | S63255057 | 10/1988 |
| JP | H0231967 | 2/1990 |
| JP | H02102659 | 4/1990 |
| JP | H0528351 | 2/1993 |
| JP | H0645671 | 2/1994 |
| JP | H06121499 | 4/1994 |
| JP | H0938198 | 2/1997 |
| JP | H10512946 | 12/1998 |
| JP | H11500941 | 1/1999 |
| JP | H1147272 | 2/1999 |
| JP | 2000279527 | 10/2000 |
| JP | 2000514671 | 11/2000 |
| JP | 2001104486 | 4/2001 |
| JP | 2002505927 | 2/2002 |
| JP | 2002516160 | 6/2002 |
| JP | 2003047272 | 2/2003 |
| JP | 2003518984 | 6/2003 |
| JP | 2006500076 | 1/2006 |
| JP | 2007500039 | 1/2007 |
| JP | 2009539562 | 11/2009 |
| WO | WO9206732 | 4/1992 |
| WO | WO9516480 | 6/1995 |
| WO | WO9617190 | 6/1996 |
| WO | WO9623158 | 8/1996 |
| WO | 09726931 | 7/1997 |
| WO | WO9723255 | 7/1997 |
| WO | WO9726931 | 7/1997 |
| WO | WO9822178 | 5/1998 |
| WO | WO9942166 | 8/1999 |
| WO | WO0006230 | 2/2000 |
| WO | WO0044419 | 8/2000 |
| WO | WO03084832 | 10/2003 |
| WO | WO2005023355 | 3/2005 |
| WO | 2007146586 | 12/2007 |
| WO | WO2008051647 | 5/2008 |
| WO | 2009112838 | 9/2009 |
| WO | 2009143116 | 11/2009 |
| WO | 2011008689 | 1/2011 |
| WO | 2011062767 | 5/2011 |
| WO | 09723255 | 12/2011 |
| WO | 2014014602 | 1/2014 |
| WO | 2014153302 A1 | 9/2014 |

OTHER PUBLICATIONS

Notice of Allowance dated Aug. 21, 2020 for U.S. Appl. No. 16/229,469 (pp. 1-5).
Notice of Allowance dated Jun. 17, 2020 for U.S. Appl. No. 16/229,469 (pp. 1-5).
Notice of Allowance dated Sep. 10, 2020 for U.S. Appl. No. 16/164,229 (pp. 1-9).
Notice of Allowance dated Feb. 14, 2011 for European Patent Application No. 05722427.1 (6 pages).
Office Action dated Feb. 10, 2023 for U.S. Appl. No. 16/666,870 (pp. 1-7).
Office Action dated Jun. 7, 2011 for Canadian Patent Application No. 2,553,335 (4 pages).
Ong et al., Prospective Randomized Comparative Evaluation of Proximal Valve Polyurethane and Distal Valve Silicone Peripherally Inserted Central Catheters, (Aug. 2010), 1191-1196.
Pittiruti et al., A Prospective, Randomized Comparison of Three Different Types of Valved and Non-Valved Peripherally Inserted Central Catheters, pp. 519-523. (1999).
Poli et al., A Comparative Study on the Mechanical Behavior of Polyurethane PICCs, pp. 175-181. (2016).
Ricchezza et al., A Strategy for Reducing Catheter Occlusions and Infections: The Experience at St. Joseph's Hospital, (2009).
Rivitz et al., "Power injection of peripherally inserted central catheters," J. Vasc. Interv. Radiol., vol. 8, No. 5, pp. 357-863 (1997).

(56) References Cited

OTHER PUBLICATIONS

Rogalla et al., Safe and easy power injection of contrast material through a central line, Eur. Radiol., vol. 8, No. 1, pp. 148-149 (1998).
Roth et al., "Influence of radiographic contrast media viscosity to flow through coronary angiographic catheters," Cathet. Cardiovasc. Diagn., vol. 22, No. 4, pp. 290-294 (1991) 5 pages.
Saito et al., "Diagnostic brachial coronary arteriography using a power-assisted injector and 4 French catheters with new shamps," J. Invasive Cardiol., vol. 9, No. 7pp. 461-468 (1997).
Walsh et al., "Effect of contrast agent viscosity and injection flow velocity on bolus injection pressures for peripheral Venous injection in first-pass myocardial perfusion studies," Technol. Health Care, vol. 10, No. 1, pp. 57-63 (2002).
Williamson et al., "Assessing the adequacy of peripherally inserted central catheters for power injection of intravenous contrast agents for CT," J Comput. Assist. Tomogr., vol. 25, No. 6, pp. 932-937 (2001).
Asch, "Venous access: options, approaches and issues," Can. Assoc. Radiol. J., vol. 52, No. 3, pp. 153-164 (2001) 12 pages.
Aw et al., Incidence and Predictive Factors of Symptomatic Thrombosis Related to Peripherally Inserted Central Catheters in Chemotherapy Patients, (2012), pp. 323-326.
Burns, The Vanderbilt PICC Service: Program, Procedural, and Patient Outcomes Successes, (2005), pp. 1-10, vol. 10 No. 4.
Carlo et al., A prospective Randomized Trial Demonstrating Valved Implantable Ports Have Fewer Complications and Lower Overall Cost Than Nonvalved Implantable Ports, (Aug. 7, 2004), pp. 722-727.
Carlson, et al., Safety Considerations in the Power Injection of Contrast Media Via Central Venous Catheters During Computed Tomographic Examinations, Investigative Radiology vol. 27, 1992, pp. 337-340.
Chahoud et al., "Randomized comparison of coronary angiography using 4F catheters: 4F manual versus 'Acisted' power injection technique," Catheter Cardiovasc. Interv., vol. 53, No. 2, pp. 221-224 (2001).
Corrected Notice of Allowability dated Oct. 27, 2020 for U.S. Appl. No. 16/164,229 (pp. 1-6).
elastomer. (2003). In The Macmillan Encyclopedia. Basingstoke, Hampshire: Macmillan Publishers Ltd. Retrieved Feb. 23, 2009 from http://www.credoreference.com/entry/3298087/.
English Translation of Office Action dated Aug. 18, 2009 for Japanese Patent Application No. 2006-517107 (3 pages).
English Translation of Office Action dated Jan. 28, 2011 for Japanese Patent Application No. 2006-517107 (3 pages).
English Translation of Office Action dated Mar. 29, 2010 for Japanese Patent Application No. 2006-517107 (2 pages).
Examination Report dated Apr. 6, 2006 for European Patent Application No. 04751644.8 (5 pages).
Examination Report dated Aug. 12, 2010 for European Patent Application No. 05722427.1 (6 pages).
Examination Report dated Mar. 26, 2010 for European Patent Application No. 05722427.1 (5 pages).
Extended Search Report dated Sep. 21, 2011 for European Patent Application No. 11173038.8 (5 pages).
Herts et al., "Power injection of contrast media using central venous catheters: feasibility, safety, and efficacy," AJR Am. J. Roentgenol., vol. 176, No. 2, pp. 447-453 (2001) 8 pages.
Herts et al., "Power injection of intravenous contrast material through central venous catheters for CT: in vitro evaluation," Radiology, vol. 200, No. 3, pp. 731-735 (1996).
Hoffer et al., Peripherally Inserted Central Catheters with Distal versus Proximal Valves: Prospective Randomized Trial, Society of Interventional Radiology, pp. 1173-1177, vol. 12 No. 10, Oct. 2001.
Hoffer et al., Prospective Randomized Comparison of Valved Versus Nonvalved Peripherally Inserted Central Vein Catheters, pp. 1393-1398, May 1999.
International Search Report PCT-US-05-011244—ISR dated Jun. 6, 2005.
International Preliminary Report on Patentability dated Jan. 3, 2006 for International Application No. PCT/US2004/014344 (7 pages).
International Preliminary Report on Patentability dated Jul. 31, 2006 for International Application No. PCT/US2005/001244 (8 pages).
International Preliminary Report on Patentability dated Nov. 232010 for International Application No. PCT/US2009/044468 (7 pages).
International Search Report 10800375_SESR dated Jul. 10, 2014.
International Search Report 10800375-7_ESO dated Jul. 17, 2017.
International Search Report 11158827-3_ESO dated May 19, 2011.
International Search Report 11158827—ESR dated May 11, 2011.
International Search Report and Written Opinion dated Dec. 23, 2009 for International Application No. PCT/US2009/044468 (10 pages).
International Search Report and Written Opinion dated Jun. 6, 2005 for International Application No. PCT/US2005/001244 (12 pages).
International Search Report and Written Opinion dated Nov. 5, 2004 for International Application No. PCT/US2004/014344 (9 pages).
International Search Report and Written Opinion dated Sep. 3, 2010 for International Application No. PCT/US2010/041698 (10 pages).
International Search Report PCT-US-05-000761 IPRP dated Jul. 31, 2006.
International Search Report PCT-US-05-000761 ISR dated Dec. 4, 2005.
International Search Report PCT-US-05-000761—WOSA dated Jul. 29, 2006.
International Search Report PCT-US-05-001244 IPRP dated Jul. 31, 2006.
International Search Report PCT-US-09-044468 IPRP dated Nov. 23, 2010.
International Search Report PCT-US-09-044468 ISR dated Dec. 23, 2009.
International Search Report PCT-US-09-044468—WOSA dated Nov. 25, 2010.
International Search Report PCT-US-10-041698 ISR dated Sep. 2009.
International Search Report PCT-US-10-041698—ISR dated Dec. 2010.
International Search Report PCT-US10-041698 IPRP dated Jan. 17, 2012.
International Search Report PCT-US10-041698—IPRP dated Nov. 17, 2012.
Johnston et al., The Effect of Peripherally Inserted Central Catheter (PICC) Valve Technology on Catheter Occlusion Rates—The 'ELeCTRiC' Study, (2012), pp. 421-425.
Kaste et al., "Safe use of power injectors with central and peripheral venous access devices for pediatric CT," Pediatr. Radiol., vol. 26, No. 8, pp. 449-501 (1996).
McMahon, Evaluating New Technology to Improve Patient Outcomes, pp. 250-255, vol. 25, No. 4, Jul./Aug. 2002.
Moureau, Nancy L., Glenda L. Dennis, Elizabeth Ames, and Robyn Severe. "Electrocardiogram (EKG) Guided Peripherally Inserted Central Catheter Placement and Tip Position: Results of a Trial to Replace Radiological Confirmation ." Journal of the Association for Vascular Access 15.1 (2010): 8-14. Web.
Notice of Allowance dated Jan. 25, 2023 for U.S. Appl. No. 17/115,347 (pp. 1-5).
Notice of Allowance dated Sep. 28, 2022 for U.S. Appl. No. 17/115,347 (pp. 1-8).

\* cited by examiner

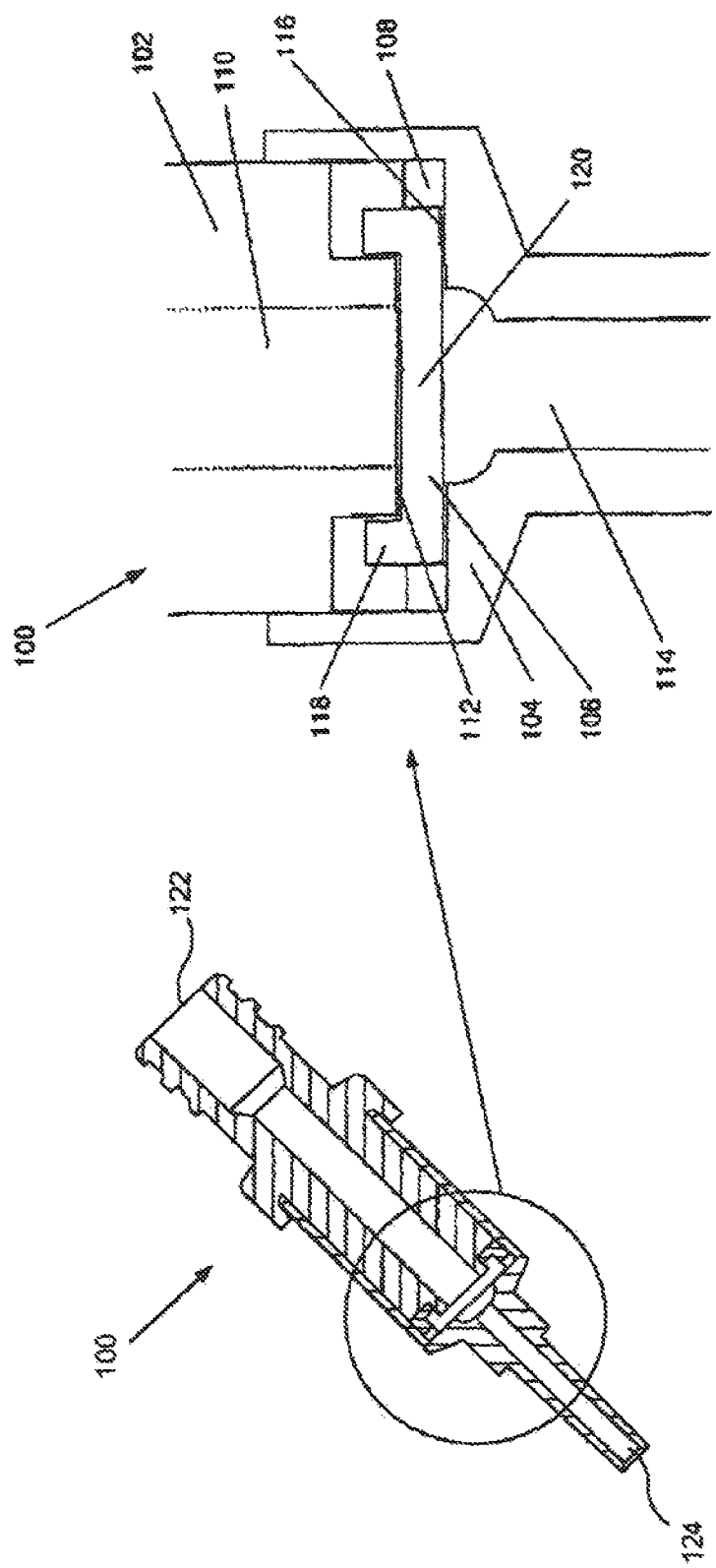

PRESSURE ACTIVATED VALVE FOR HIGH FLOW RATE AND PRESSURE VENOUS ACCESS APPLICATIONS

BACKGROUND

Pressure activated safety valves may be incorporated into medical devices such as peripherally inserted central catheters (PICCs), ports, dialysis catheters and tunneled central catheters which provide long term access to the vascular system. Pressure activated safety valves generally include a slitted, flexible disk extending across a lumen. The flexible disk is generally constructed so that, when subjected to a threshold fluid pressure, edges of the slit separate from one another to permit flow through the lumen. When the pressure applied to the disk drops below the threshold level, the slit reseals to prevent leakage from or to the vascular access device. It would be desirable at times to employ within these vascular access devices fluid pressures in excess of the pressures to which these known flexible membranes have been traditionally exposed to with hand injections (e.g., when flushing an obstructed lumen, administering high-flow rate fluids, etc.).

SUMMARY OF THE INVENTION

The present invention is directed to a valve comprising a first housing including a first lumen extending therethrough and defining a first disk-facing surface and a second housing including a second lumen extending therethrough and defining a second disk-facing surface, the second housing being mated to the first housing so that the second disk-facing surface faces the first disk-facing surface in combination with a flexible disk gripped between gripping portions of the first and second disk-facing surfaces, the disk including a slit extending therethrough which, when acted upon by a fluid pressure of at least a predetermined threshold level opens to permit fluid flow between the first and second lumens and which, when acted upon by a fluid pressure less than the threshold level remains sealed preventing fluid flow between the first and second lumens.

BRIEF DESCRIPTION OF THE DRAWINGS

FIG. 1 shows a section view of a device, according to a first exemplary embodiment of the present invention;

FIG. 2 shows an enlarged view of the device of FIG. 1;

DETAILED DESCRIPTION

Figure 3:
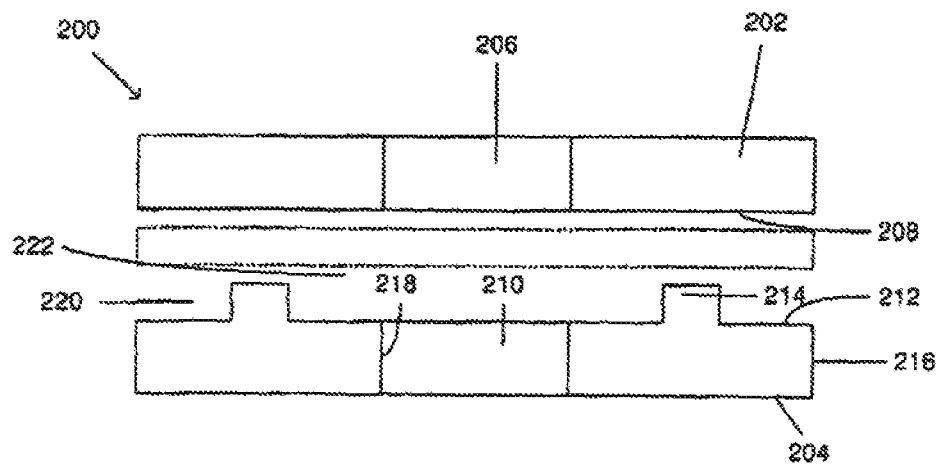
FIG. 3 shows a cross-sectional side view of capture area of a device, according to a second exemplary embodiment of the present invention.

The present invention may be further understood with reference to the following description and the appended drawings, wherein like elements are referred to with the same reference numerals. The present invention relates to apparatus for controlling fluid flow through medical devices specifically for sealing devices which remain in place in the body to provide long term access to the vascular system. To improve the performance of pressure activated safety valves, embodiments of the present invention include features for fixing a disk and tuning the valve performance to withstand the increased pressures and flow rates associated with certain procedures.

As described in more detail below, exemplary embodiments of the present invention provide features for enhancing the performance of a pressure activated valve including a feature fixing a slitted, flexible disk in a desired position, a relief well to accommodate portions of the flexible disk moved out of the fixation area and a sit bias feature creating a bias aiding in tuning the performance of the valve (e.g., to select a threshold activation pressure).

As shown in FIGS. 1 and 2, a device 100 according to a first exemplary embodiment comprises a first housing 102 and a second housing 104 coupled to one another to hold a disk 106 therebetween. The device 100 may further comprise an additional capture component 108, such as an o-ring. As shown in FIG. 1, the first housing 102 may, for example, be located at a proximal end 122 of the device 100 while the second housing 104 may be located at a distal end 124 of the device 100. As shown in FIG. 2, the first housing 102 includes a lumen 110 extending therethrough and a disk-facing surface 112. The second housing 104 includes a lumen 114 extending therethrough and a disk-facing surface 116. It will be understood by those of skill in the art that the first housing 102 and the second housing 104 are brought together to hold a disk 106 therebetween such that a pressure activated sit in the disk is positioned between the lumens 110, 114 to control fluid communication therebetween. A circumference of the disk-facing surface 112 of the first housing 102 and the disk-facing surface 116 of the second housing may be substantially the same as a circumference of the disk 106 so that the first housing 102, the second housing 104 and the disk 106 are substantially aligned within the device 100.

The disk 106 may, if desired, operate as a bidirectional valve allowing fluid flow through the device 100 in either direction. Alternatively, the disk 106 may be structured or, one or both of the first and second housings 102, 104, respectively, may include a structure preventing the disk 106 from deforming in one direction and opening to permit fluid flow through the valve in that direction. Thus, fluid flow would be permitted only in the other direction. Fluid may be being administered to the body via the device 100 when a fluid pressure applied to the proximal end 122 of the device 100 exceeds a threshold value at which the disk 106 deforms so that the slit of the disk 106 opens to permit fluid flow therethrough to the distal end 124 of the device 100. So long as the fluid pressure remains at least as great as the threshold level, the slit remains open and fluid passes through the disk 106 and the lumen 112 to the body. Fluid may be withdrawn from the body when a negative fluid pressure applied to the proximal end 122 exceeds the threshold level deforming the disk 106 and the slit thereof proximally to permit fluid flow from the distal end 124 of the device 100 to the proximal end 122 thereof. The fluid may be drawn from the body through the lumen 112 of the second housing 104. This fluid flow will be maintained so long as the fluid pressure remains at least the threshold value. As soon as the fluid pressure applied against the disk 106 in either direction drops below the threshold level, the disk 106 returns to the sealed configuration in which edges of the slit therethrough abut one another preventing fluid flow therethrough.

The disk 106 may be flexible such that the disk 106 may be held between the first housing 102 and the second housing 104 in a substantially planar configuration or in a deformed configuration, as shown in FIG. 2. The capture component 108, shown as an o-ring, may be housed between the first housing 102 and the second housing 104 such that when the disk 106 is held between the disk-facing surface 112 and the disk-facing surface 116, an outer edge 118 of the disk 106 is deformed so that an outer edge 118 extends away from a plane of a central portion 120 of the disk 106 into a relief well 420 formed around a circumference of the disk facing surface 112 of the first housing 102. If it is desired to have a substantially neutral valve (i.e., a valve with substantially equal threshold pressure levels regardless of the direction of now), the disk-facing surfaces and, between which the disk 106 is fixed, may be formed substantially planar to hold the central portion 120 in place without bending it in one direction or the other. It will be understood by those of skill in the art, however, that other factors such as diameter, may also affect the tuning of the valve. In addition, either or both of those portions of the disk-facing surfaces contacting the disk 106 and forming fixation features of the first and second housings 102, 104, respectively, may be coated, textured, covered or overmolded with a thermoplastic elastomer or thermoset plastic such as silicone to enhance the coefficient of friction to aid in valve disk retention during high now applications.

In another embodiment, the disk 106 may be non-planar. For example, rather than a planar surface as shown in FIG. 2, the disk 106 may have a concave or convex shape. It will be understood by those of skill in the art, however, that the disk 106 may take a variety of other non-planar shapes and forms so long as the disk 106 may be fixed between the first housing 102 and the second housing 104. It will also be understood by those of skill in the art that the disk 106 may include more than one slit which may be pressure activated. Additionally, either of or both of the first and second housings 102, 104, respectively, may include more than one lumen extending therethrough. With flow through each of these lumens controlled by separate slits or by one or more common slits extending across multiple lumens.

The following alternate embodiments, shown in FIGS. 3-14, are substantially the same as the device 100 described above, but may include alternate geometrical aspects forming the fixation feature, the relief well and the slit bias. For example, the first and second housings of the following embodiments align such that the lumen of the first housing is in fluid communication with the lumen of the second housing with a flexible disk secured therebetween so that a slit of the disk is positioned between the lumens to control fluid flow therebetween. Additionally, the figures show a capture area of the device in which the disk would be held such that the device is depicted via surfaces of a distal portion of the first housing and a proximal portion of the second housing.

Figure 4:
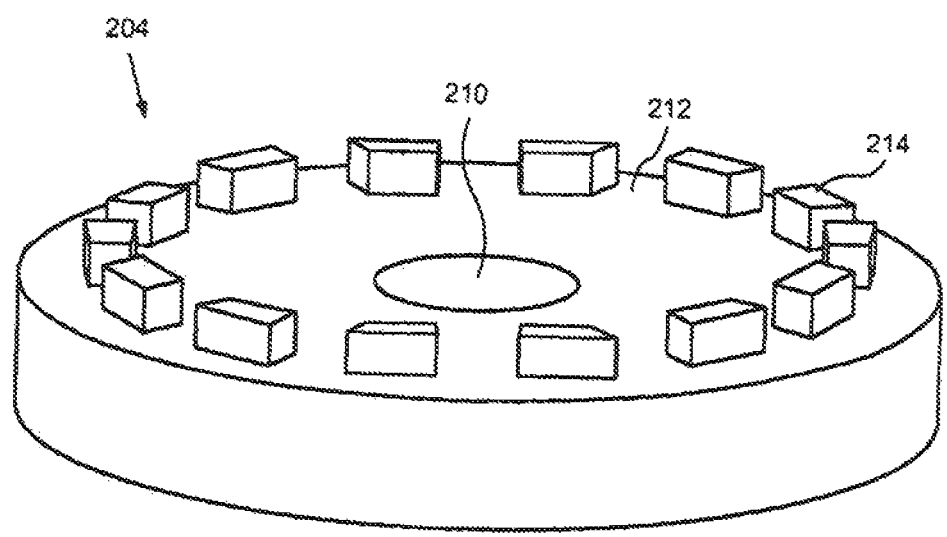
FIG. 4 shows a perspective view of a portion of a second housing of the device of FIG. 3, according to a further embodiment.
Figure 5:
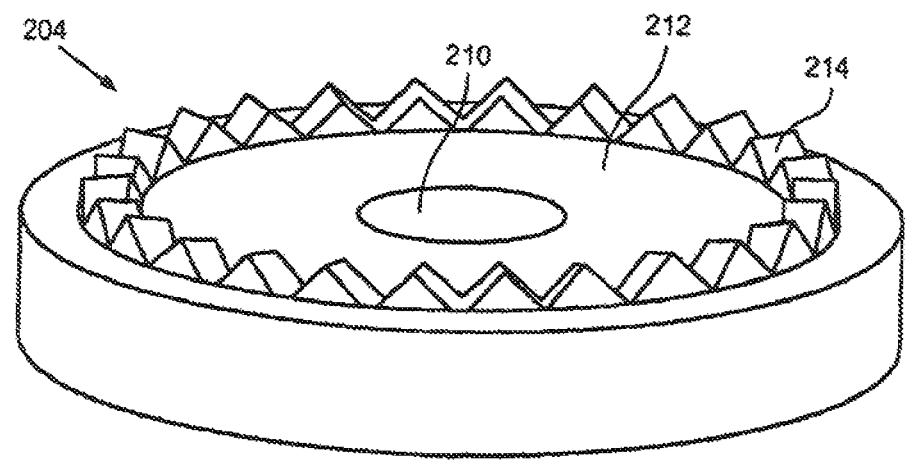
FIG. 5 shows a perspective view of a portion of the second housing of the device of FIG. 3, according to an alternate embodiment.

As shown in FIG. 3, a device 200, according to another embodiment of the present invention comprises a first housing 202 and a second housing 204 for securing a disk (shown in broken lines) therebetween. The first housing 202 includes a lumen 206 extending therethrough and a surface 208, which faces a disk received in the space between the first and second housings 202, 204, respectively. The surface 208 may be substantially planar so that an entire area thereof contacts the disk. The second housing 204 includes a lumen 210 extending therethrough and a surface 212 facing the space in which the disk will be received. The surface 212 may further include at least one protrusion 214 forming a fixation feature pressing against the surface 208 a portion of the disk abutting thereagainst. The protrusion 214 may be formed as an annular ring encircling the lumen 210 radially within an outer circumference 216 of the second housing 204 with a circumference greater than an inner circumference of a wall 218 of the lumen 210. The protrusion 214 be formed by a continuous ring on the disk-facing surface 208 or, in an alternative embodiment, the protrusion 214 may be formed as a series of projections extending discontinuously around the lumen 210 (e.g., as a series of arcs extending along a curve around the lumen 210. For example, as shown in FIG. 4, the non-continuous ring shape may be formed by a series of castellated teeth of the disk-facing surface 208 of the second housing 204. In another embodiment, as shown in FIG. 5, the non-continuous protrusion 214 may be formed by a series of saw teeth. Such non-continuous geometries provide localized areas of grip on the disk. It will be understood by those of skill in the art that the protrusion 214 may be formed by any variety of geometrical shapes.

A space 220 radially outside the protrusion 214 (i.e., between the protrusion 214 and the outer circumference 216) forms a relief well into which a radially outer portion of the flexible disk will extend, substantially unsecured and enabled to flex accommodating the vibrations associated with high pressure fluid flow through the slit. Additionally, a space 222 radially within the protrusion 214 would allow a central portion of the disk, including the slitted portion, to flex toward the second housing 204, until the central portion of the disk contacts the surface 212. Thus, the device 200 will be able to withstand increased fluid pressures when fluid flows through the device in a positive direction (from the first to the second housing). It will be understood in the art, however, that the slit is not biased in any particular direction when there is no fluid flow through the device 200. Those skilled in the art will also understand that the designation of the first housing 202 as upstream (i.e., proximal) of the second housing 204 is exemplary only and may be reversed as may the location of the protrusion 214. That is, the second housing 204 may be formed as either the proximal or distal end of the valve of the device 200 and the protrusion 214 may be formed on either of the first and second housings 202, 204, respectively, in either the proximal or the distal of the two.

Figure 6:
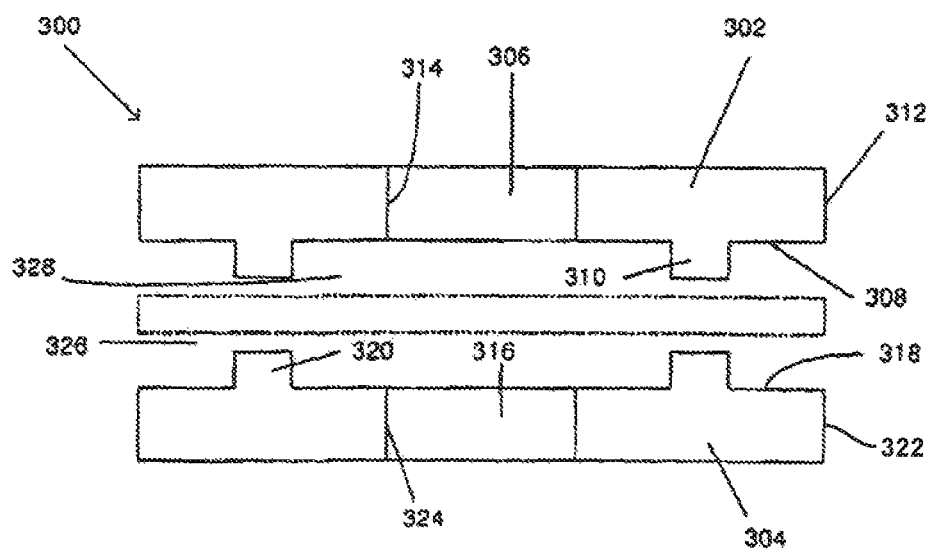
FIG. 6 shows a cross-sectional a side view of a capture area of a device, according to a third embodiment of the present invention.

According to another embodiment of the present invention, as shown in FIG. 6, a device 300, comprises a first housing 302 and a second housing 304 for holding a flexible disk (shown in broken lines) therebetween. The device 300 is substantially similar to the device 200, described above with the first housing 302 including a lumen 306 extending therethrough and a surface 308 which faces a space in which a disk will be received. The surface 308 includes a protrusion 310, which may extend around the lumen 306 continuously or non-continuously as described above in regard to device 200. As described above in regard to the protrusion 214, the protrusion 310 has a circumference less than that of an outer circumference 312 of the first housing 302 but greater than an inner circumference 314 of the first housing 302 which forms the lumen 306. The second housing 304 includes a lumen 316 extending therethrough and a surface 318 which faces the space within which a disk will be received. The device 300 differs from the device 200, however, in that the surface 318 also includes a protrusion 320 which extends either continuously or discontinuously about the lumen 316. A circumference of the protrusion 318 is less than an outer circumference 322 of the second housing 304 but greater than an inner circumference 324 of the second housing 304 which forms the lumen 316. It will be understood by those of skill in the art that the protrusion 310 of the first housing 302 preferably substantially aligns with the protrusion 320 of the second housing 304 such that a disk held therebetween is gripped by the first and second housings 302, 304, respectively, with the protrusions 310 and 320 pressing portions of the disk inward toward one another. Thus, the protrusions 310, 320 form a fixation feature which holds the disk therebetween.

When the protrusions 310, 312 are aligned to hold the disk therebetween, a space 326 radially outside the protrusions 310, 320 forms a relief well allowing an outer portion of the disk to remain substantially unsecured therein to flex in either direction (i.e., toward the first housing 302 or toward the second housing 304) to accommodate the vibrations associated with high pressure fluid flow. A space 328 formed radially within the protrusions 310, 320 (i.e., between the protrusions 310, 320 and the lumens 306, 316) allows a central portion of the disk, including the slitted portion, to flex to accommodate high pressure fluid flow. In other words, the central portion of the disk may flex toward the first housing 302 until the disk contacts the disk-facing surface 308 and/or toward the second housing 304 until the disk contacts the disk-facing surface 318. Thus, it will be understood by those of skill in the art that the space 328 allows the disk to accommodate a high pressure fluid flow in either direction. However, it will also be understood by those of skill in the art, that when there is no fluid flow through the device 300, the disk need not be biased in any particular direction, either positive or negative.

Figure 7:
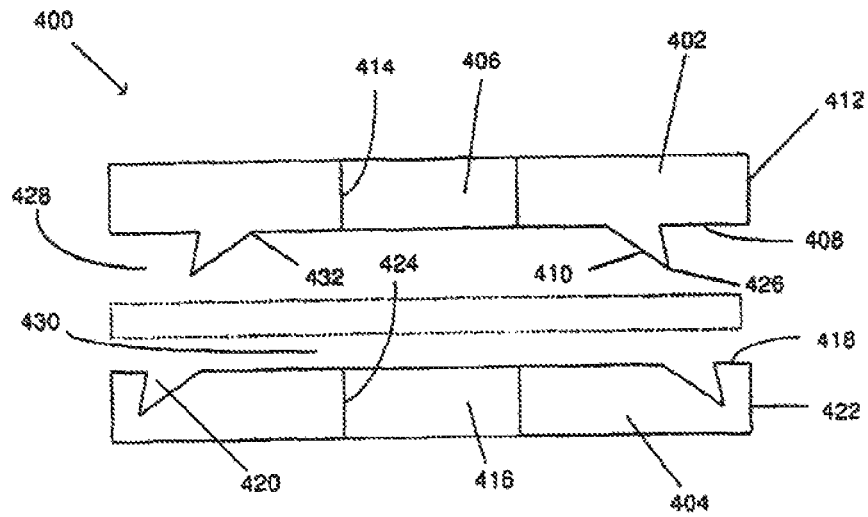
FIG. 7 shows a cross-sectional side view of a capture area of a device, according to a fourth embodiment of the present invention.
Figure 8:
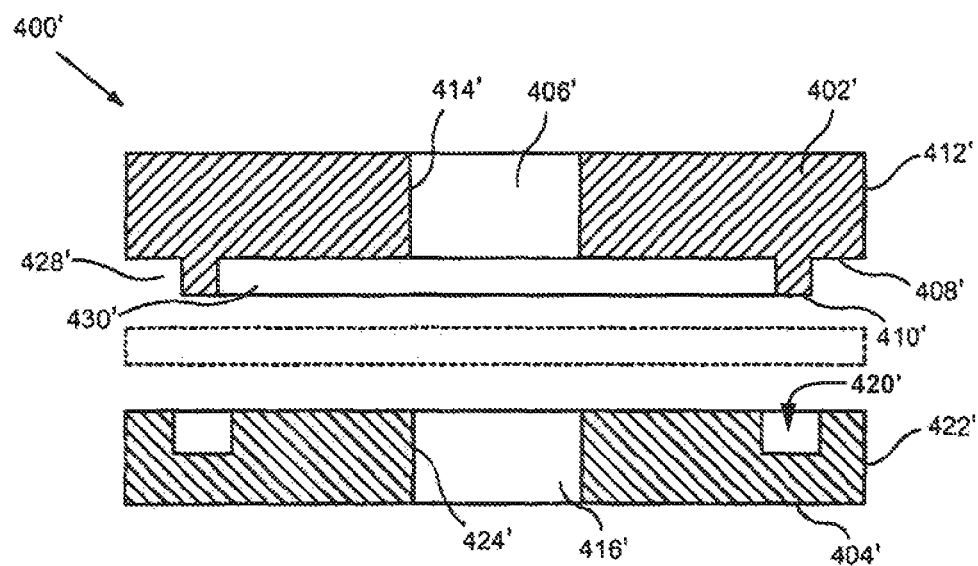
FIG. 8 shows a cross-sectional side view of a capture area of the device of FIG. 7, according to an alternative embodiment.

As shown in FIGS. 7 and 8, a device 400, according to another embodiment of the present invention, comprises a first housing 402 and a second housing 404 for holding a flexible disk (shown in broken lines) therebetween. The first housing 402 includes a lumen 406 extending therethrough and a disk-facing surface 408 which includes a protrusion 410 extending from the surface 408. The protrusion 410 extends around the lumen 406 either continuously or non-continuously in the same manner described above radially within an outer circumference 412 of the first housing 402 and radially outside an inner circumference 414 of the first housing 402 which forms the lumen 406. An outer annular space between the outer circumference 412 and the protrusion 410 forms a relief well 428 while an annular space between the protrusion 410 and the inner circumference 414 forms a relief well 430. The protrusion 410 may also include a pointed tip 426, as shown in FIG. 7. The protrusion 410 may also be angled such that the pointed tip 426 is offset radially outward from a proximal end 432 at which the protrusion 410 meets the surface 408. It will be understood by those of skill in the art that the pointed tip 426 may provide an improved grip of the disk 106 over a flat-surfaces protrusion 410.

The second housing 404 includes a lumen 416 extending therethrough and forms a disk-facing surface 418 radially outside the lumen 416. The disk-facing surface 418 optionally includes an indentation 420 (or a series of indentations 420 if the protrusion 410 is non-continuous) corresponding to a shape of the protrusion 410 formed on the first housing 402 and angled similarly thereto. Thus, portions of a disk received between the first and second housings 402, 404, respectively, and pinched by the protrusion(s) 410 will be pushed into the indentation(s) 420, locking the disk in position with a slit therethrough aligned with the lumens 406 and 416 while the relief wells 428 and 430 allow for flexing of the disk and the accommodation of vibrations under high pressure fluid flow. Alternatively, a device 400 may include only a protrusion 410 without a corresponding indentation 420 and the same modification may be made to any of the devices 400, 400' and 400" described below.

Alternatively, a device 400' as shown in FIG. 8 may include a protrusion 410' and a corresponding indentation 420' (or a series of non-continuous protrusions 410' and indentations 420') without the pointed tip of the device 400. Specifically, as shown in FIG. 8, the protrusion(s) 410' and the indentation(s) may be substantially rectangular in cross-section to form similar radially outer and inner relief wells 428' and 430', respectively, in this case, a portion of a disk received between the first and second housings 402', 404', respectively, will be pushed by the protrusion(s) 410' into the indentation(s) 420', locking the disk in position with a slit therethrough aligned with the lumens 406' and 416' and so that the relief wells 428' and 430' allow for flexing of the disk and the accommodation of vibrations under high pressure fluid flow.

Figure 9:
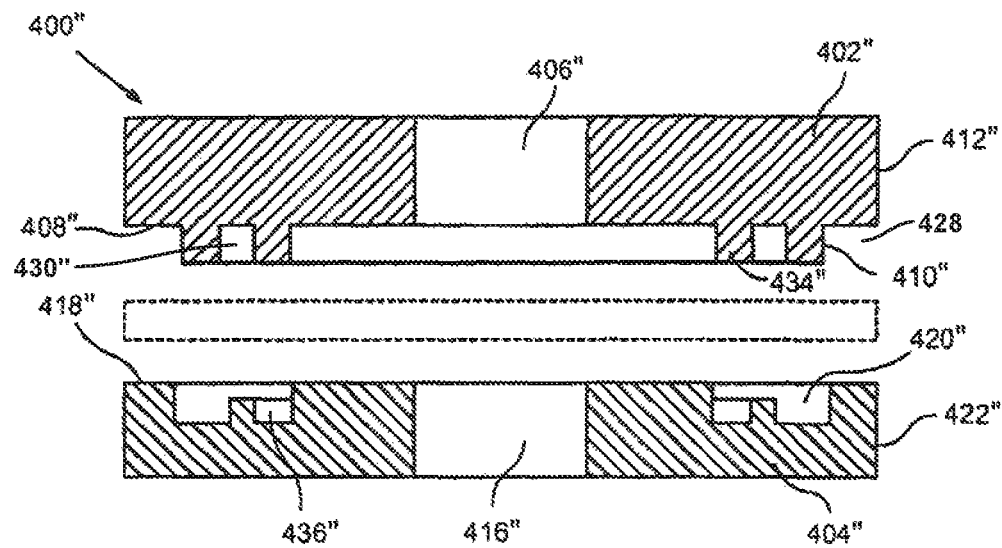
FIG. 9 shows a cross-sectional side view of a capture area of the device of FIG. 8, according to a further embodiment.

In a further embodiment of the device 400" as shown in FIG. 9 is constructed in substantially the same manner as the device 400' except that the first housing 402" includes a second protrusion 434" on a disk facing surface 408" thereof which may be either continuous or non-continuous in the same manner described above for the protrusions of the previous embodiments while the second housing 404" includes a second indentation 436" on a disk-facing surface 418" thereof which may correspond in shape and position to the second protrusion 434". The device 400" defines a radially outer relief well 428" between the first protrusion 410 and an outer circumference 412" of the first housing 402" and a radially inner relief well 430" between the second protrusion 434" and the lumen 406". It will be understood by those of skill in the art that the first and the second housings 402, 404, respectively may include any number of protrusions and indentations as desired to more secure retain a disk gripped therebetween.

Figure 10:
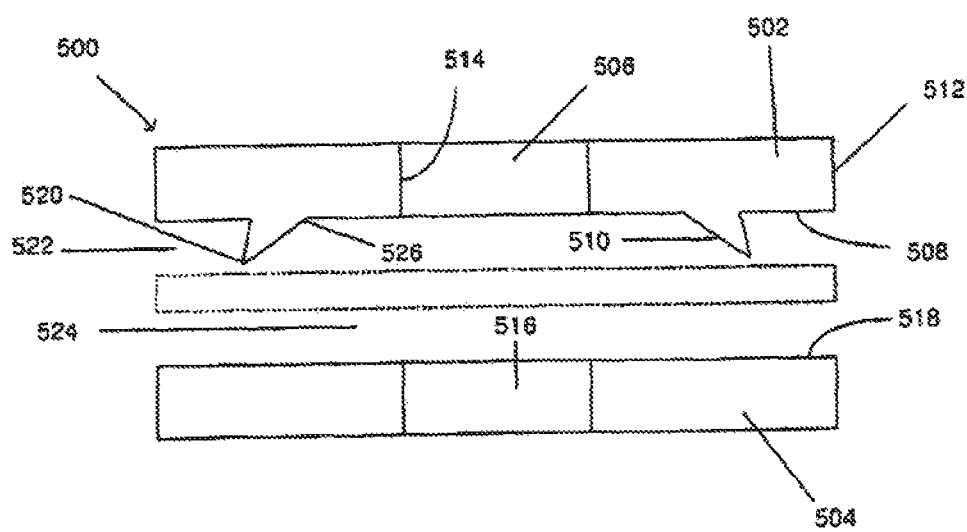
FIG. 10 shows a cross-sectional side view of a capture area of a device, according to a fifth embodiment of the present invention.

As shown in FIG. 10, a device 500, according to another embodiment of the present invention, comprises first and second housings 502, 504, respectively include disk facing surfaces 508, 518 respectively for holding a flexible disk therebetween. The device 500 is substantially similar to the device 400, as described above except that, while the disk-facing surface 508 includes a protrusion 510 shaped and positioned substantially similarly to the projection 410 shown in FIG. 7, the disk-facing surface 518 of the second housing 504 includes no corresponding indentation and, in this case, is substantially planar such that, when a flexible disk is positioned between the first and second portions 502, 504, respectively, with a slit thereof aligned with the lumens 506 and 516, portions of the disk contacting the protrusion (s) 510 are pinched against the flat surface 518 locking the disk in position while radially outer and inner relief wells 522, 524, respectively, allow for flexing of the disk and the accommodation of vibrations under high pressure fluid flow.

Figure 11:
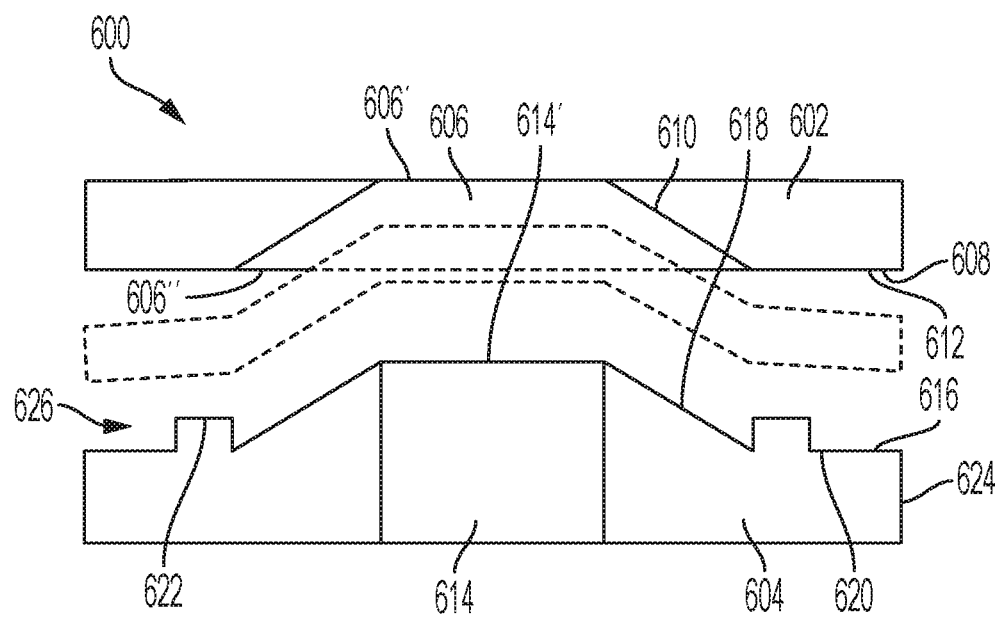
FIG. 11 shows a cross-sectional side view of a capture area of a device, according to a sixth embodiment of the present invention.

According to another exemplary embodiment shown in FIG. 11, a device 600 comprises a first housing 602 and a second housing 604 for holding a flexible disk (shown in broken lines) therebetween. The first housing 602 includes a lumen 606 extending therethrough and a disk-facing surface 608. The disk-facing surface 608 includes an inner portion 610 immediately surrounding the lumen 606 and an outer portion 612 extending radially from the inner portion 610 at a distal end of the lumen 606. The outer portion 612 may be substantially planar and oriented in any desired relationship to an axis of the lumen 606 (e.g., substantially perpendicular thereto). The inner portion 610 is angled such that a proximal opening 606' of the lumen 606 is smaller than a distal opening 606" thereof. That is, in this embodiment, the lumen 606 is substantially conical flaring outward distally.

The second housing 604 includes a lumen 614 extending therethrough to a proximal disk-facing surface 616. The lumen 614 may for example be substantially cylindrical and approximately equal in diameter to the proximal opening 606' of the lumen 606. The disk-facing surface 616 includes a radially inner portion 618 separated from a radially outer portion 620 by a protrusion 622 which may be formed as described in regard to any of the above embodiments. The inner portion 618 is angled so that, when the first and second housings 602, 604, respectively, are mated to one another with a slitted, flexible disk gripped therebetween, it is substantially parallel to the inner portion 610 of the first housing 602. Furthermore, as would be understood by those skilled in the art, although distal opening 606" is wider than the proximal opening 614', the flexible disk (shown in broken lines) will preferably have a slit which is no wider than the opening 614' and which, when gripped between the first and second housings 602, 604, respectively, will be entirely radially within the opening 614' so that fluids will pass from the lumen 606 to the lumen 614 without leaking along the inner portion 618.

As in the above-described embodiments, the protrusion 622 extends continuously or non-continuously around the lumen 614 separated therefrom by the inner portion 618 and separated from an outer circumference 624 of the second housing 604 by an annular space forming a relief well 626. It will be understood in the art that when the first and the second housings 602, 604, respectively, are mated together to secure a flexible disk therebetween, the flexible disk will bend to accommodate the angled inner portions 610, 618 with a portion of the flexible disk secured between the outer portions 612, 620 fixed to the outer portion 612 of the disk-facing surface 608 by the protrusion 622. Additionally, it will be understood by those of skill in the art that in order to accommodate the angled inner portions 610, 618 a central portion of the disk, including the slitted portion, bends in a proximal direction.

Figure 12:
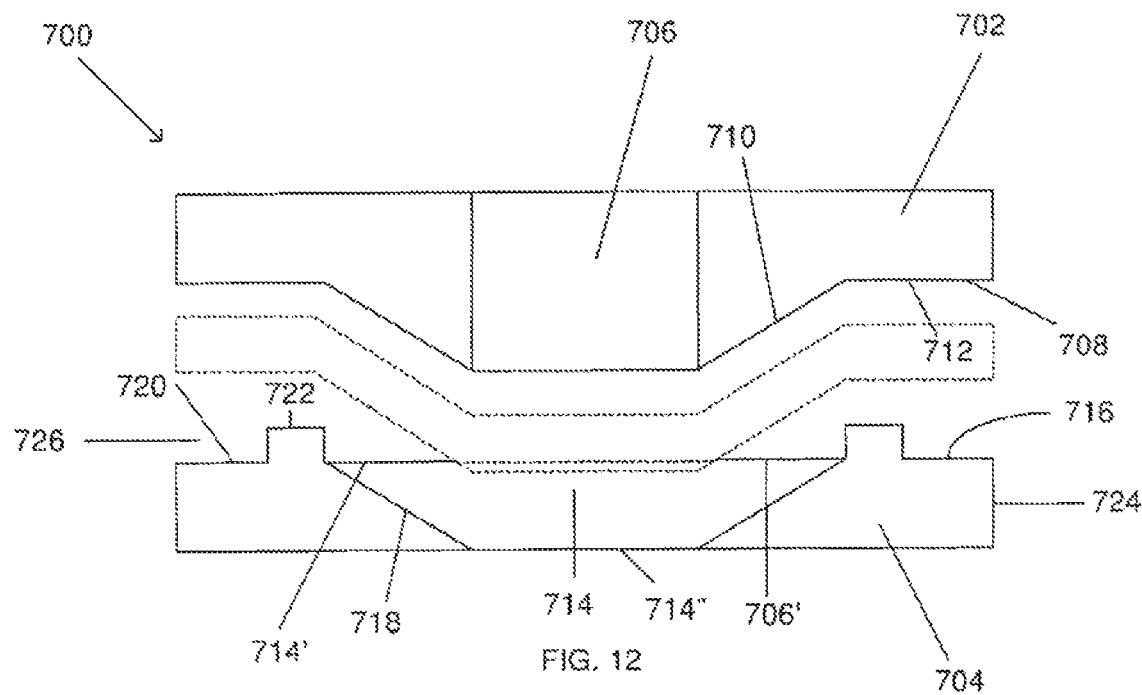
FIG. 12 shows a cross-sectional side view of a capture area of a device, according to a seventh embodiment of the present invention.

As shown in FIG. 12, a device 700 according to another embodiment of the invention comprises a first housing 702 and a second housing 704 for holding a flexible disk (shown in broken lines) therebetween. The first housing 702 includes a lumen 706 extending therethrough to a distal opening 706' surrounded by a disk-facing surface 708. An inner portion 710 of he disk-facing surface 708 is substantially conical, angling proximally away from the opening 706' to meet a substantially planar outer portion 712 extending radially outward therefrom. The second housing 704 includes a substantially conical lumen 714 extending therethrough from a proximal opening 714' to a smaller distal opening 714". The proximal opening 714' is surrounded by a disk-facing surface 716 separated from the opening 714' by a protrusion 722. The inner portion 718 comprises a wall immediately surrounding the lumen 714 and is shaped, for example, to correspond to the shape of the inner portion 710 of the first housing 702. That is, in this embodiment, the inner portion 718 is angled such that the lumen 714 is recessed relative to the outer portion 720. As in the previously described embodiments, the protrusion 722 may extend continuously or non-continuously around the opening 714' within an outer circumference 724 of the second housing 704 to define a relief well 726 within which will be received a radially outer portion of a slitted, flexible disk to be gripped between the first and second housings 702, 704, respectively. As described above, the disk will be pinched between the projection 722 and the outer portion 712 and between the inner portions 710 and 718 leaving the radially outer portion of the disk free to vibrate when exposed to high flow rates.

As will be understood by those of skill in the art, the flexible disk will bend to accommodate the angled inner portions 710, 718 of the disk facing surfaces 708, 716 creating a positive slit bias reducing the pressure required for flow proximal to distal as compared to that required for flow from the distal to the proximal.

Figure 13:
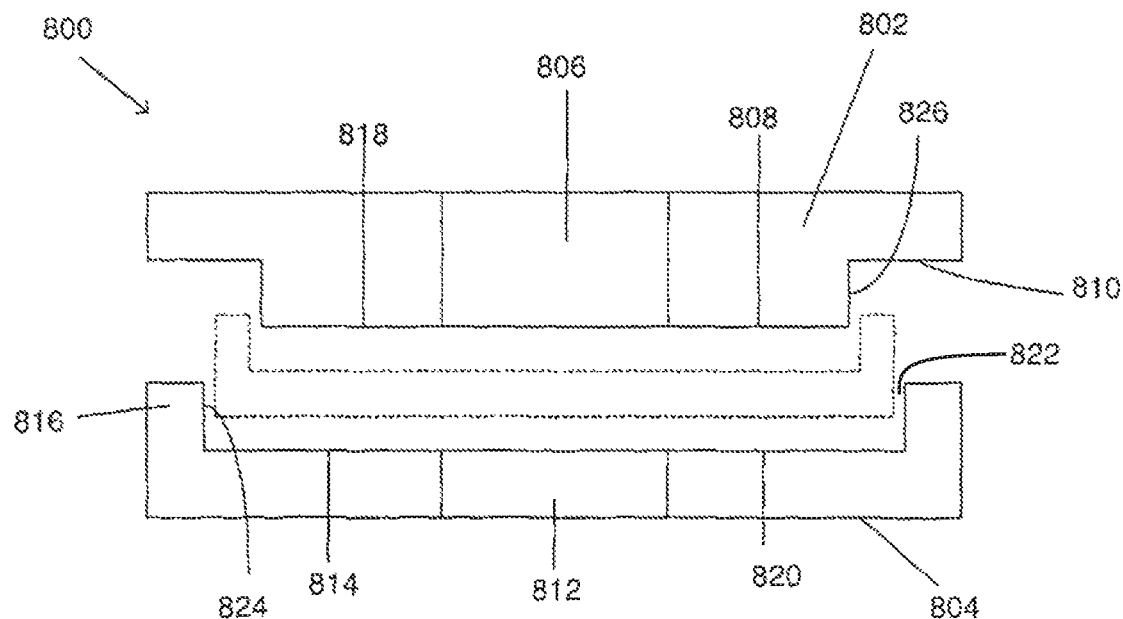
FIG. 13 shows a cross-sectional side view of a capture area of a device, according to an eighth embodiment of the present invention.

As shown in FIG. 13, a device 800 according to another embodiment of the invention comprises a first housing 802 and a second housing 804 for holding a flexible disk (shown in broken lines) therebetween. The first housing 802 includes a lumen 806 extending therethrough and a disk-facing surface 808 including a recessed portion 810 extending around an outer-most perimeter of the disk-facing surface 808. That is, a portion of the first housing 802 radially outside the disk-facing surface 808 is recessed away from the second housing relative to the disk-facing surface 808. The second housing 804 includes a lumen 812 extending therethrough and a disk-facing surface 814 which includes a non-continuous or continuous protrusion 816 as described above extending around an outer-most perimeter of the disk-facing surface 814. A radially inner surface of the protrusion 816 is radially further from the lumens 806, 812 than the outer perimeter of the disk-facing surface 808 so that an annular gap extends there between when the first housing 802 is coupled to the second housing 804 with a flexible disk gripped therebetween. It will be understood by those of skill in the art that although the protrusion 816 is described as formed on the disk-facing surface 814 of the second housing 804, an o-ring may be included in the device 800 as an alternative to the protrusion 816. In this alternative embodiment, the o-ring may be placed between the first and the second housings 802, 804 when the disk is being fixed therebetween in substantially the same position described for the protrusion 816.

A circumference of the disk-contacting portion 818 of the disk-facing surface 808 may be smaller than a circumference of the protrusion 816 on the disk-facing surface 814 such that when the first and second housing 802, 804 are mated, a relief well 822 is formed by an annular space between an inner surface 824 of the protrusion 816 and an outer surface 826 of the disk-contacting portion 818. The disk may be fixed between the first and the second housings 802, 804, respectively, such that the disk-contacting portion 818 secures the disk to a disk-contacting portion 820 of the disk-facing surface 814 radially within the protrusion 816. It will be understood by those of skill in the art that the disk may be positioned therebetween such that the disk is substantially planar or, in the alternative, such that outer edges of the disk are deformed, as shown in FIG. 13, by the protrusions 816. Thus, an unsecured radially outer portion of the disk may flex within the relief well 822 to accommodate high pressure fluid flow therethrough. As the remaining portion of the disk is firmly secured between the disk-contacting portion 818 and the disk-contacting portion 820, it will be understood by those of skill in the art that the a neutral slit bias exists, meaning that, in this embodiment, the device 800 opens to permit flow from proximal to distal at substantially the same threshold pressure as it opens to permit flow from distal to proximal.

Figure 14:
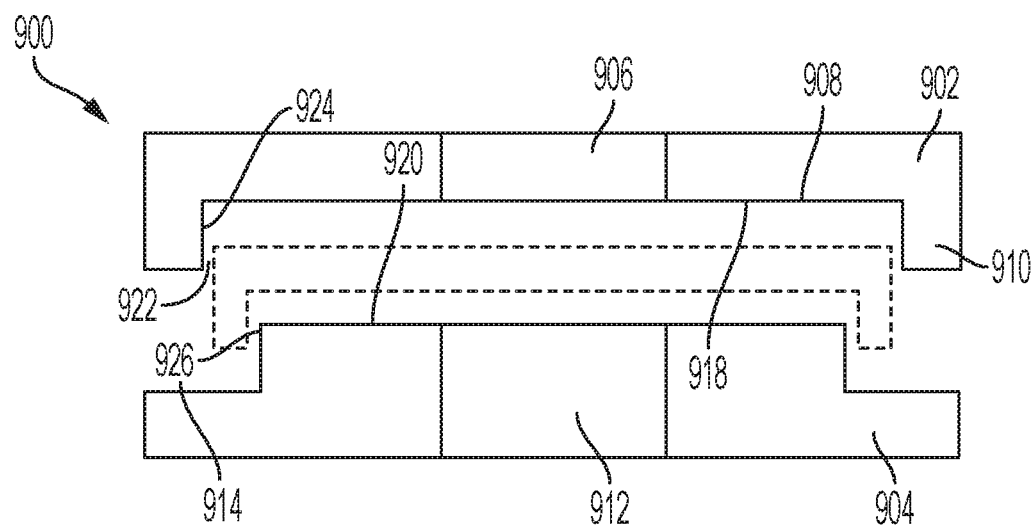
FIG. 14 shows a cross-sectional side view of a capture area of a device, according to a ninth exemplary embodiment of the present invention.

As shown in FIG. 14, a device 900 according to another embodiment of the invention comprises a first housing 902 and a second housing 904 for securing a flexible disk (shown in broken lines) therebetween. The device 900 is substantially similar to the device 800 described above except that the first housing 902 includes a protrusion 910 extending continuously or non-continuously around an outer-most perimeter of a disk-facing surface 908 as described above while the second housing 904 includes a recessed portion 914 extending around an outer-most perimeter of a disk-facing surface, radially outside a disk contacting portion 920 of the disk-facing surface 914. Similarly to the device 800, the first housing 902 includes a lumen 906 extending therethrough while the second housing 904 includes a lumen 912 extending therethrough. A circumference of the disk-contacting portion 920 of the disk facing surface 914 is smaller than a circumference of the protrusion 910 on the disk-facing surface 908 such that, when the first and second housing 902, 904, respectively, are mated to one another, a relief well 922 is formed by an annular space between an inner surface 924 of the protrusion 910 and an outer surface 926 of the disk-contacting portion 920. Thus when a disk is fixed between the first and the second housings 902, 904, respectively, with the disk contacting portion 920 securing the disk to a disk-contacting portion 918, an outer edge of the disk is free to flex within the relief well 922 when a high pressure fluid flow passes therethrough. Similarly, it will be understood by those of skill in the art that although the protrusion 910 is described as formed on the first housing 902, an o-ring may be included in the device 900 in place of the protrusion 910 between the first and the second housings 902, 904, respectively, in the same position occupied by the protrusion 910.

It will be apparent to those skilled in the art that various modifications and variations can be made in the structure and the methodology of the present invention, without departing from the spirit or scope of the invention. For example, in any of the embodiments any of the features mentioned for a first housing may be moved to a second housing and vice versa. In addition, features mentioned with respect to controlling flow in the distal to proximal direction may be reversed to obtain the same effect in proximal to distal flow and vice versa. Thus, it is intended that the present invention cover any modifications that come within the scope of the appended claims and their equivalents.

The invention claimed is:

1. A device comprising:
    a first housing comprising a first housing lumen, a first housing protrusion, and a first housing relief well; wherein the first housing relief well is positioned radially outward relative to the first housing protrusion;
    a second housing comprising a second housing protrusion and a second housing relief well; wherein the second housing relief well is positioned radially outward relative to the second housing protrusion;
    a flexible disk comprising a valve;
    wherein the first housing protrusion extends continuously around the first housing lumen;
    wherein the first housing relief well or the second housing relief well accommodate movement of a periphery of the flexible disk as a result of fluid flow through the valve; and
    wherein the first housing relief well defines a first space between the flexible disk and the first housing, and the second housing relief well defines a second space between the flexible disk and the second housing.

2. The device of claim 1, wherein at least a section of the periphery of the flexible disk is configured to flex into the first housing relief well and the second housing relief well to accommodate movement associated with the fluid flow through the valve.

3. The device of claim 2, wherein the second housing protrusion extends continuously around the second housing lumen.

4. The device of claim 3, wherein the valve comprises at least one slit valve.

5. The device of claim 4, wherein the at least one slit of the flexible disk comprises at least two slits; and wherein the movement of the flexible disk as a result of the fluid flow is configured to open at least one of the at least two slits.

6. The device of claim 1, wherein the first housing is coupled to the second housing.

7. The device of claim 1, wherein the first housing protrusion and the second housing protrusion are substantially aligned; and wherein the first housing protrusion and the second housing protrusion are configured to secure the flexible disk therebetween.

8. The device of claim 1, wherein the first and second housings secure the flexible disk therebetween.

9. A device comprising:
    a first housing comprising a first housing lumen, a first housing protrusion, and a first housing relief well; wherein the first housing relief well is positioned radially outward relative to the first housing protrusion;
    a second housing comprising a second housing protrusion and a second housing relief well; wherein the second housing relief well is positioned radially outward relative to the second housing protrusion;
    a flexible disk comprising at least one slit and a periphery radially outward from the at least one slit;
    wherein the first housing protrusion extends continuously around the first housing lumen;
    wherein either the first housing relief well or the second housing relief well accommodate movement of the periphery of the flexible disk as a result of fluid flow through the at least one slit between the first housing lumen and the second housing lumen; and
    wherein the first housing relief well substantially aligns with the second housing relief well.

10. The device of claim 9, wherein at least a part of the flexible disk is compressed between the first housing protrusion and the second housing protrusion.

11. The device of claim 10, wherein the flexible disk is comprised of silicone.

12. The device of claim 11, wherein at least a section of the flexible disk periphery is configured to deform or flex into either the first housing relief well or the second housing relief well as a result of the fluid flow.

13. The device of claim 10, wherein the at least one slit of the flexible disk opens upon a threshold activation pressure.

14. The device of claim 13, wherein the at least one slit of the flexible disk comprises at least two slits; and wherein the movement of the flexible disk as a result of the fluid flow is configured to open at least one of the at least two slits.

15. A device comprising:
   a first housing comprising a first housing protrusion, a first housing lumen, and a first housing relief well; wherein the first housing relief well is positioned radially outward relative to the first housing lumen and the first housing protrusion;
   a second housing comprising a second housing protrusion, a second housing surface, a second housing lumen, and a second housing relief well; wherein the second housing relief well is positioned radially outward relative to the second housing lumen and the second housing protrusion;
   a flexible disk having a central slit and an annular end extending about a periphery of the flexible disk, wherein the central slit is configured to allow fluid flow between the first and second lumens, and wherein the annular end is configured to flex or deform within at least one of the first or second relief wells in response to fluid flow through the central slit between the first and second lumens.

16. The device of claim 15, wherein the second housing protrusion continuously extends around the second housing lumen.

17. The device of claim 15, wherein the first housing protrusion has a circumference less than that of the first housing relief well.

18. The device of claim 17, wherein the second housing protrusion has a circumference less than that of the second housing relief well.

19. The device of claim 18, wherein the first and second housings secure the flexible disk therebetween.

20. The device of claim 19, wherein the first housing relief well substantially aligns with the second housing relief well.

* * * * *